United States Patent [19]

Yoritomi

[11] Patent Number: 4,604,199
[45] Date of Patent: Aug. 5, 1986

[54] FILTERING COLUMN

[75] Inventor: Kenzaburo Yoritomi, Chibashi, Japan

[73] Assignee: Suomen Sokeri Oy, Espoo, Finland

[21] Appl. No.: 721,792

[22] Filed: Apr. 10, 1985

[30] Foreign Application Priority Data

Apr. 12, 1984 [JP] Japan ................................ 59-073299

[51] Int. Cl.⁴ ............................................ B01D 23/18
[52] U.S. Cl. ..................................... 210/293; 210/292
[58] Field of Search ............... 210/293, 264, 279, 285, 210/286, 287, 288, 289, 266, 792–794, 290, 291

[56] References Cited

U.S. PATENT DOCUMENTS 3,468,422  9/1969  Camp ................................. 210/293
3,956,134  5/1976  Sturgill .............................. 210/293
4,118,322 10/1978  Roman .............................. 210/293

Primary Examiner—Frank Sever
Attorney, Agent, or Firm—Brumbaugh, Graves, Donohue & Raymond

[57] ABSTRACT

A filtration column having a bottom with reciprocally arranged peaks and troughs. Branched pipes with uniformly distributed small holes on their lower portions and surrounded by screens or wedge pipes lie in the troughs. The branched pipes lead to gathering pipes, which in turn lead to an outlet.

5 Claims, 4 Drawing Figures

FILTERING COLUMN

BACKGROUND OF THE INVENTION

The present invention relates generally to a filtering column having a filtering media containing a special bottom and multiple branched pipes as collectors.

Filtering reaction columns are well known for use in processes for separation of components in a feed solution, for example for use in ion exchange resin reactions and as reactors for immobilized enzymes. These columns generally have large diameters in order to maximize column capacity, but as diameter increases it is difficult to maintain uniform flow through a column cross-section.

Uniform flow is critical for efficient use of these columns. Recently, in order to produce better uniform flow, the use of flat bottoms has been recommended in ion exchange resin columns. The use of columns with a flat bottom has also been proposed for continuous chromatographic separation processes similar to those processes disclosed in U.S. Pat. No. 4,267,054. In the latter case, several filtering columns may be used, connected by a pipe line, and the liquid must flow uniformly through the cross-section of each column, without back mixing and without dead space between columns.

In the past, filtering columns have had filtering media constructed with a layer of silicic sand, or a large number of strainers, on a perforated plate. Liquid is filtered through these media, collected on a spherical panel, and flows out from the center of the panel. This type of structure is undesirable because the flow tends to "short cut," i.e., to be greater, at the center of the column than at the periphery, and also dead spaces exist at the spherical panel which cause undesirable back mixing.

In an attempt to reduce these problems, filtering columns have been manufactured with a plurality of branched pipes distributed uniformly on the flat bottom of the column, the pipes having small holes on their undersides and being covered by a filtering screen. These branched pipes connect to gathering pipes, which take fluids to an outlet. However, this structure can still result in back mixing and non-uniform flow, as illustrated in FIG. 1.

FIG. 1, which is labeled "PRIOR ART," is a side sectional view of a part of the flat bottom of the column previously described, illustrating two branched pipes 1 on the flat bottom 4. The branched pipes 1 have small holes 3 at their undersides, and are covered by a filtering screen 2. The course of the liquid flow is illustrated by the arrows.

It is clear that the course of the flow down to the point between the two branched pipes 1 is longer than the course of flow straight to the branched pipes 1. Since these two courses do not have the same distance, the liquid flow into the branched pipe 1 is mixed with two kinds of flow, which are former and later inleted liquids. In other words, the fluid entering pipes 1, from the two different flow paths, is a mixture of fluid from two different heights in the column. This is known as back mixing. Also, the point 5 at the center of the two branched pipes 1 is a dead spot in the flow. This known structure thus does not collect liquid maintaining a uniform flow through the filtering column.

BRIEF SUMMARY OF THE INVENTION

The present invention is an improved filtration column. The filtering column has a bottom with reciprocally arranged peaks and troughs. Branched pipes with uniformly distributed small holes in their lower portions and screens or wedge wire pipes surrounding them lie in the troughs. The branched pipes lead to gathering pipes, which in turn lead to an outlet. Consequently, liquids pass through the screens into the branched pipes, flow to the gathering pipes, and then pass through an outlet.

Preferably, in columns of larger cross-section, the bottom area of the filtering column is divided into several blocks, each having the same area. The centers of all the blocks are connected together symmetrically through the gathering pipes to direct the filtrates to the center of each block, and the center collection points of the respective blocks are connected together symmetrically to direct the filtrates to the center of the column and thereafter to the outlet. This structure allows for uniform flow through the cross-section of the filtering column.

DETAILED DESCRIPTION

Figure 1:
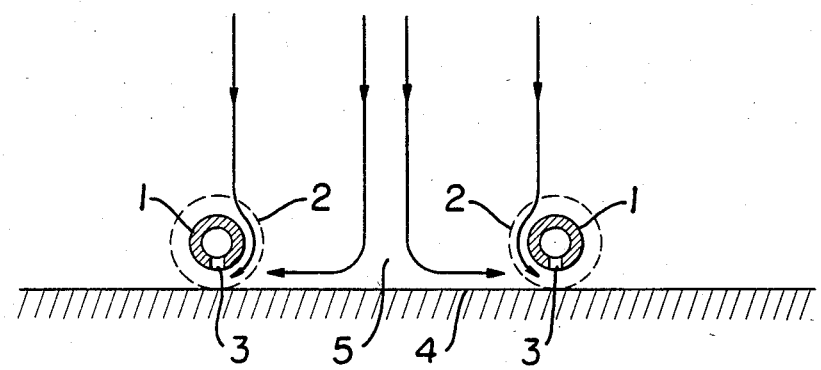
FIG. 1 is a side, sectional view of a portion of a prior art filtering column removal system.

While this invention is susceptible of embodiment in many different forms, there is shown in the drawings and will herein be described in detail a preferred embodiment, with the understanding that the present disclosure is to be considered as an exemplification of the principles of the invention and is not intended to limit the invention to the embodiment illustrated.

Figure 2:
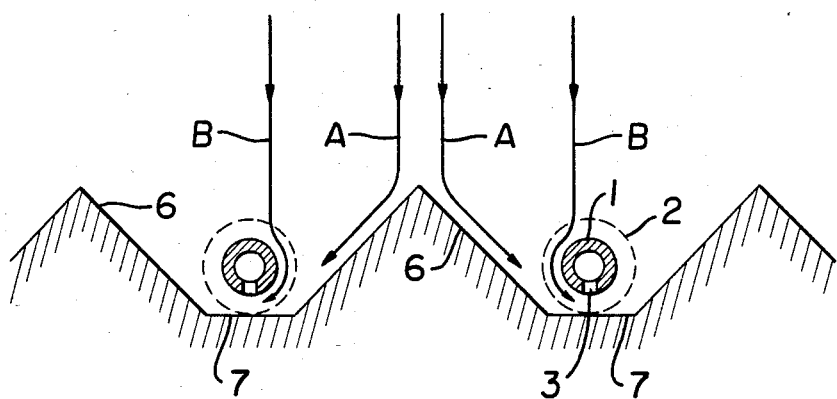
FIG. 2 is a side, sectional view of a bottom portion of a filtering column in accordance with this invention.

FIG. 2 of the drawings illustrates the bottom of a column that may be of the known types referred to in the background section. However, unlike known columns, the bottom is formed by reciprocally arranged peaks 6 and troughs 7, spaced at constant intervals, as shown in FIG. 2. The branched pipes 1 lie in the troughs 7. These branched pipes 1 each have small holes 3 uniformly distributed on their underside and are covered with a filtering screen 2. The fluid flow direction is indicated by arrows. Unlike the structure shown in FIG. 1, which has dead spaces 5, the peaks 6 channel the fluid flow A into the trough 7 so that no dead spaces exist on the bottom of the filtering column. Also, the flow distance of the filtrate A to the inlets 3 is substantially the same as the flow distance of the filtrate B to the inlets 3, thus achieving uniform fluid flow across the width of the column.

Preferably, the peaks 6 are at least as high as the top of the filtering screen 2 and the peaks 6 and troughs 7 are of the shape which provides no restrictions, i.e., a smooth fluid flow to the branched pipes 1. Preferably, the projections are formed by flat plates. Also, the troughs 7 are shaped and have an appropriate width, for providing liquid flow smoothly to the branched pipes. The branched pipes are positioned in a manner which allows the filtrates to be collected uniformly, and allow fluids to be drawn to the outlet through the gathering pipes so that only slight differences exist in the length of flow courses.

The branched pipes in the present invention have three characteristics:

1. The length of the pipes is limited so that back mixing is prevented therein.
2. The pipes are uniformly distributed and cover the entire bottom of the column.
3. The holes in the undersides of the pipes are uniformly distributed and the number and diameter are selected according to the desired liquid flow rate.

Figure 3:
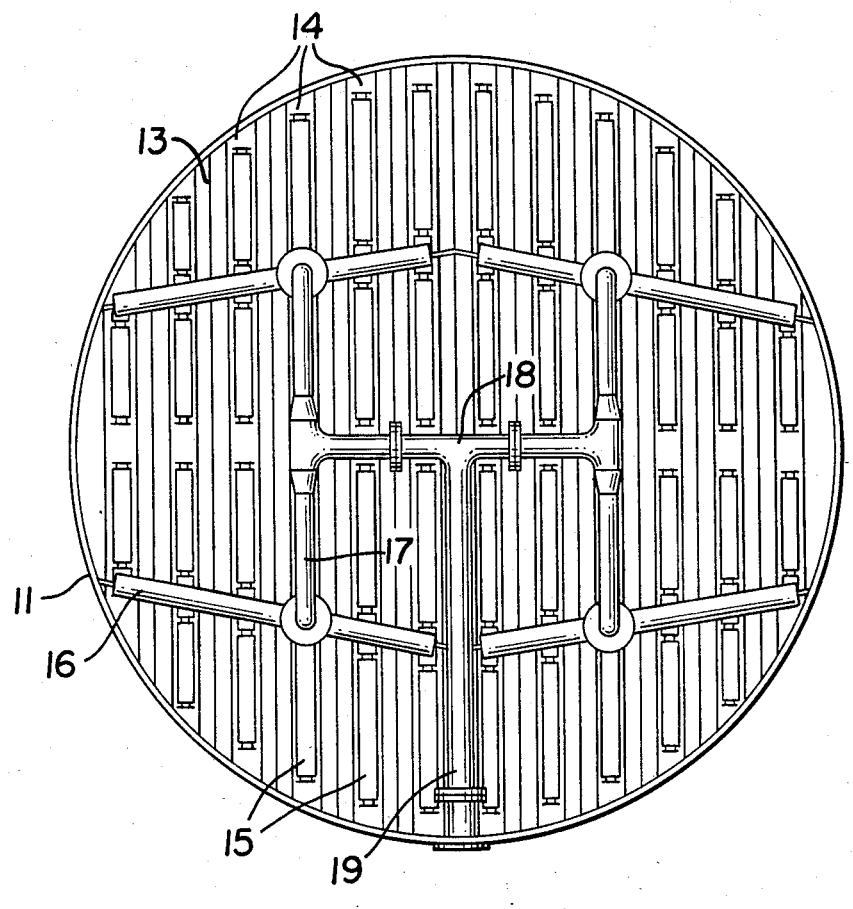
FIG. 3 is a plan view of one embodiment of a filtering column utilizing the bottom construction shown in FIG. 2.
Figure 4:
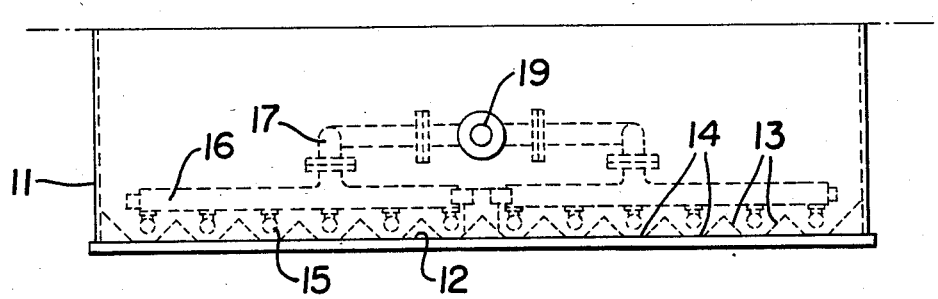
FIG. 4 is a side view of the filtering column shown in FIG. 3.

In large scale columns having large diameters, uniform flows are difficult to obtain. Consequently, an embodiment of the present invention, as shown in FIGS. 3 and 4, is preferred. The bottom of the filtration column 12 is divided into several blocks, having the same area, in which the branched pipes 15 are installed. This division into blocks allows the branched pipes to be limited to a certain length, thus keeping the amount of back mixing within a limited range. Each branched pipe 1 is connected to the first series of gathering pipes 16, which in turn lead to the center of each block. The center of each block is connected symetrically to the second series of gathering pipes 17 which lead to another gathering pipe 18, leading to the center of the column, and then to an outlet 19. While FIG. 3 shows a filtration column with four blocks, additional blocks may be provided in various embodiments.

The above-identified structure for a filtration column is simple in construction, low in cost, achieves a uniform flow rate even if the diameter of the column is large and may be adapted to large scale industrial apparatus.

EXAMPLE

The present invention was employed in a chromatographic separator as found in U.S. Pat. No. 4,267,054, Example 4, the four column system. In that system, the diameter of the columns was 3.0 meters, the height of the peaks was 100 mm and the pitch (distance between the peaks) of the projections or branched pipes was 240 mm. The results of a pulse flow test on this structure with a sugar solution show a peak of the sugar solution between the eluant water very sharp compared with the past apparatus. This indicates that the flow in the columns of the present invention is uniform and back mixing is minimum. In actual running, fractionation is significantly improved.

I claim:
1. A filtering column which comprises:
   a bottom having reciprocally arranged peaks and troughs formed therein and spaced apart at constant intervals;
   a plurality of branched pipes having small holes in their undersides uniformly therealong, said pipes lying in said troughs on the bottom;
   filter means covering said respecting branch pipes said troughs having sides sloping downwardly to said respective branched pipes to afford smooth fluid flow thereto and the sides of adjacent troughs intersecting to form said peaks;
   gathering pipes connected to said branched pipes; and
   an outlet connected to the gathering pipes said gathering pipes being connected to said branched pipes at locations such that the differences in the lengths of the flow courses from said branched pipes to said outlet are slight, such that a uniform flow rate is achieved without substantial backmixing.
2. A filtering column according to claim 1, wherein the filtering column bottom is divided into several blocks, each block having the same area.
3. A filtering column according to claim 1, wherein the gathering pipes are symetrically arranged on the bottom.
4. A filtering column according to claim 1, wherein the filter means comprises a screen surrounding each branched pipe.
5. A filtering column according to claim 1, wherein the filter means comprises a wedge wire pipe surrounding each branched pipe.

* * * * *